United States Patent [19]

Lehmann et al.

[11] Patent Number: 4,920,100
[45] Date of Patent: * Apr. 24, 1990

[54] ALKYL GYLCOSIDES AS POTENTIATING AGENTS IN ANTISEPTIC COMPOSITIONS

[75] Inventors: Rudolf Lehmann, Leichlingen; Klaus Hachmann, Hilden; Manfred Biermann, Muehlheim/Ruhr; Harald Schnegelberger, Leichlingen, all of Fed. Rep. of Germany

[73] Assignee: Henkel Kommanditgesellschaft auf Aktien, Duesseldorf-Holthausen, Fed. Rep. of Germany

[*] Notice: The portion of the term of this patent subsequent to May 31, 2005 has been disclaimed.

[21] Appl. No.: 60,137

[22] Filed: Jul. 9, 1987

[30] Foreign Application Priority Data

Jun. 9, 1986 [DE] Fed. Rep. of Germany ....... 3619375

[51] Int. Cl.$^5$ .................... A01N 61/00; A01N 31/02; A61L 2/16
[52] U.S. Cl. ........................................ 514/23; 514/25; 514/635; 514/901; 424/49; 424/55
[58] Field of Search ...................... 424/49, 55; 514/23, 514/25, 901, 635

[56] References Cited

U.S. PATENT DOCUMENTS

| 3,547,828 | 12/1970 | Mansfield et al. | 252/351 |
| 3,598,865 | 8/1971 | Lew | 260/210 R |
| 3,707,535 | 12/1972 | Lew | 260/210 R |
| 3,772,269 | 11/1973 | Lew | 260/210 R |
| 3,839,318 | 10/1974 | Manfield | 260/210 R |
| 4,198,392 | 4/1980 | Juneja | 424/48 |
| 4,349,669 | 9/1982 | Klahr et al. | 536/127 |
| 4,748,158 | 5/1988 | Biermann et al. | 514/635 |

FOREIGN PATENT DOCUMENTS 0077167 4/1983 European Pat. Off. .

Primary Examiner—Ronald W. Griffin
Attorney, Agent, or Firm—Wayne C. Jaeschke; Henry E. Millson, Jr.; Real J. Grandmaison

[57] ABSTRACT

Alkyl glycosides in admixture with bactericidally active alcohols or carboxylic acids in, e.g. aqueous treatment solutions, for potentiating the microbicidal effect thereof.

31 Claims, No Drawings

ALKYL GYLCOSIDES AS POTENTIATING AGENTS IN ANTISEPTIC COMPOSITIONS

BACKGROUND OF THE INVENTION

1. Field of the Invention

This invention relates to the use of alkyl glycosides as potentiating agents in antiseptic and disinfecting cleaning compositions containing alcohols or carboxylic acids, to enhance the bactericidal activity thereof.

2. Discussion of Related Art

Alkyl glycosides, their production and their use, particularly as surfactants, have been known for some time, see for example, U.S. Pat. Nos. 3,839,318; 3,707,535; 3,547,828; 3,598,865; 3,772,269; and 4,349,669; and also European patent application No. 0 077 167. Alkyl glycosides are readily produced by reaction of glucose or oligosaccharides with alcohols containing from 8 to 25 carbon atoms in the alkyl radical. Biodegradable surface-active materials suitable for a variety of applications are obtained in this way.

Investigations into the microbiological and, in particular, antimicrobial properties of alkyl glycosides have shown that, even in high in-use concentrations of up to 10,000 ppm, they do not develop any significant antimicrobial activity on their own. Even combinations of alkyl glycosides with quaternary ammonium compounds are unremarkable in their effects although quaternary ammonium compounds as such do show bactericidal activity. The use of alkyl glycosides in combination with quaternary ammonium compounds, as described for example in U.S. Pat. No. 3,547,828 does not in practice produce any unexpected technical benefits.

The antimicrobial activity of alcohols and carboxylic acids has also been known for some time. This activity has even been utilized in practice to a limited extent. Unfortunately, the use of alcohols or carboxylic acids in antimicrobial preparations has numerous disadvantages repeatedly encountered in practice. For example, the relatively high vapor pressure of the alcohols used in antimicrobial preparations puts at risk anybody working with such preparations. In addition, the preparations gradually lose the antimicrobial alcohol upon prolonged storage, particularly at elevated temperature. Another disadvantage repeatedly encountered is that alcohols only develop satisfactory antimicrobial activity in relatively high concentrations. In general, the alcohols have to be used in concentrations of from 20 to 30%. On the other hand, the use of carboxylic acids in antimicrobial preparations repeatedly results in unacceptable pollution of the surrounding atmosphere if they have to be used in the concentrations necessary for developing antimicrobial activity.

DESCRIPTION OF THE INVENTION

Other than in the operating examples, or where otherwise indicated, all numbers expressing quantities of ingredients or reaction conditions used herein are to be understood as modified in all instances by the term "about".

An object of the present invention is to provide simple, readily biodegradable chemical compounds which, in combination with known antimicrobial compounds, results in an increase in the activity of the antimicrobial compounds so that they can be used in reduced concentrations in antimicrobial preparations, thus lessening if not completely eliminating the disadvantages discussed above. There is also an economic need to find simple, biodegradable compounds which, in combination with the antimicrobial compounds discussed above, lead to a synergistic increase in the performance of these antimicrobial compounds, particularly with respect to certain microbicidal effects.

It has now surprisingly been found that the use of alkyl glycosides as potentiating agents in antiseptic preparations containing alcohols or carboxylic acids leads to a distinct increase in the bactericidal effect of the alcohols or carboxylic acids, which is reflected in particular in a distinct improvement in their microbicidal effect on gram-positive bacteria. Conversely, it has been possible to achieve an equally good microbicidal effect, i.e. the destruction of certain bacteria at very much lower concentrations than known from the prior art, with the immediate result that the in-use concentrations of the alcohols or carboxylic acids acting as microbicidal agents can be significantly reduced, which not only affords economic advantages, but also means that side effects and disadvantages of the type discussed above can be eliminated.

Accordingly, the present invention relates to the use of alkyl glycosides in admixture with bactericidally active alcohols or carboxylic acids in aqueous treatment solutions for potentiating the microbicidal effect of those compounds.

In addition, the invention relates to aqueous, bactericidally active disinfecting and cleaning preparations which contain activesubstance mixtures of alkyl glycosides and bactericidal alcohols or carboxylic acids.

In the context of the invention, microbicidal agents for combination with alkyl glycosides are alcohols or carboxylic acids which can be used either individually as bactericidal compounds or in the form of mixtures of several compounds belonging to the same class.

Known bactericidally active alcohols for use in accordance with the invention include aliphatic alcohols and phenyl-aliphatic alcohols, i.e. aliphatic alcohols substituted by phenyl groups in the aliphatic C-chain, which may contain one or more hydroxyl groups.

Of the aliphatic alcohols, straight-chain or branched, unsubstituted or mono- or disubstituted aliphatic alcohols containing from 1 to 6 carbon atoms in the alkyl or alkylene radical are preferably used for the purposes of the invention. One or more of the above-mentioned alcohols are mixed with alkyl glycosides in accordance with the invention. The alcohols mentioned show excellent solubility in aqueous media and, as already known, show pronounced bactericidal properties. Within the above-mentioned group, straight-chain or branched unsubstituted aliphatic alcohols containing from 2 to 4 carbon atoms in the alkyl or alkylene radical are particularly preferred. Among alcohols such as these, ethanol, n-propanol, isopropanol or mixtures thereof may be used with particular advantage, i.e develop a particularly good bactericidal effect, in admixture with alkyl glycosides.

The mono- or disubstituted aliphatic alcohols are preferably straight-chain or branched, aliphatic $C_2$–$C_4$ alcohols substituted by 1 or 2 substituents from the group Cl, Br or $NO_2$, instead of or in admixture with the above disclosed alcohols as the bactericidally active substances. Of these compounds, 2-bromo-2-nitro-1,3-propane diol, which is commercially available as "Bronopol", is particularly useful by virtue of its favorable bactericidal properties.

In another embodiment of the invention, it is also possible to use straight-chain or branched, unsubstituted or mono- or disubstituted phenyl-aliphatic alcohols containing from 1 to 3 carbon atoms in the alkylene radical instead of straight aliphatic alcohols as the bactericidally active alcohols. In the context of the invention, "phenyl-aliphatic" alcohols are understood to be alcohols in which the alcohol function is attached to the alkyl chain and the alkyl radical additionally contains a phenyl radical as substituent. Within the group of alcohols such as these, straight-chain, unsubstituted phenylaliphatic alcohols containing 1 to 3 carbon atoms in the alkylene radical or straight-chain phenyl-aliphatic alcohols containing from 1 to 3 carbon atoms in the alkylene radical substituted by 1 or 2 substituents from the group comprising Cl, Br or $NO_2$ are particularly preferred for admixture with alkyl glycosides. Benzylalcohol for example is mentioned as a particularly advantageous bactericidal alcohol belonging to this class because it shows an excellent bactericidal action in relatively low in-use concentrations.

Antimicrobially active carboxylic acids can also be mixed with alkyl glycosides for use in accordance with the invention. In this case, too, a single antimicrobially active carboxylic acid can be used in admixture with the alkyl glycosides or, alternatively, several carboxylic acids can be used in admixture with the alkyl glycosides.

The carboxylic acids used in admixture with the alkyl glycosides in accordance with the invention are, in particular, aliphatic or aromatic carboxylic acids containing one or more carboxyl groups or water-soluble salts thereof. It is preferred to use straight-chain or branched, saturated or unsaturated, unsubstituted or mono- or disubstituted aliphatic monocarboxylic or dicarboxylic acids containing from 1 to 12 carbon atoms either individually or in admixture with one another. Water-soluble salts of these carboxylic acids can also be used in accordance with the invention. Within the above-mentioned group, straight-chain or branched unsubstituted aliphatic monocarboxylic acids containing from 3 to 6 carbon atoms and water-soluble salts thereof are preferably used by virtue of their high solubility in water and their known antimicrobial activity. Of these monocarboxylic acids, propionic acid, butyric acid, valeric acid or water-soluble salts thereof can be used with particular advantage, i.e. develop good bactericidal activity even in comparatively low concentrations, in admixture with alkyl glycosides.

However, one or more carboxylic acids (or water-soluble salts thereof) from the group comprising straight-chain or branched, mono- or poly-olefinically unsaturated aliphatic monocarboxylic acids containing from 3 to 6 carbon atoms can also be used in admixture with alkyl glycosides in accordance with the invention. Within this group, sorbic acid or water-soluble salts thereof are used with particular advantage in admixture with alkyl glycosides; the bactericidal and preserving effect of sorbic acid being well known.

Straight-chain or branched, saturated or unsaturated aliphatic carboxylic acids containing from 3 to 6 carbon atoms which are substituted by 1 or 2 substituents from the group Cl, Br, $NO_2$ and OH, or water-soluble salts thereof, can also be used in admixture with alkyl glycosides. Within this group, lactic acid is of particular importance.

In another advantageous embodiment of the invention, unsubstituted, monocyclic aromatic carboxylic acids or monocyclic aromatic carboxylic acids substituted by 1 or 2 substituents from the group Cl, Br and OH, or salts thereof, are used in admixture with alkyl glycosides as bactericidally active compounds. In this embodiment, too, the above compounds can be used in admixture with the alkyl glycosides either individually or in the form of mixtures with one another. Within the group of these compounds, preferred are benzoic acid, salicylic acid and water-soluble salts thereof which, as is known, show bactericidal activity even in comparatively low concentration, and can also be used in the antimicrobial preparations of the invention.

The water-soluble salts of the antimicrobially active carboxylic acids, which are also usable in accordance with the invention are primarily alkali metal salts, of which the sodium salts are preferably used in practice by virtue of their ready availability.

The surprising advantage of using alkyl glycosides in admixture with the bactericidally active alcohols or carboxylic acids in accordance with the invention lies in the fact that, where the antimicrobially active compounds are used in the usual concentrations, the microbicidal effect is developed much more quickly by addition of alkyl glycosides or in the fact that, alternatively, the concentrations normally used can be considerably reduced to achieve an equally good bactericidal effect. Under this particular aspect of the invention, it is surprisingly possible to considerably reduce the quantities used in practice and at the same time to readily eliminate the economic disadvantages and the disadvantages involved in using the corresponding preparations, such as their high vapor pressure, the pungent odor of the compounds, etc. In addition, it is possible by using the alkyl glycosides, which are readily biodegradable as such, to specifically enhance or rather potentiate the antimicrobial effect of the alcohols or carboxylic acids, while leaving the effect of other constituents totally unaffected.

Where the alkyl glycosides are used under the first-discussed aspect of the invention for accelerating the antimicrobial effect of the bactericidally active alcohols and carboxylic acids, the alcohols and carboxylic acids are used in their typical known concentrations. If, by contrast, the alkyl glycosides are to be used under the second aspect of the invention as mentioned above, the bactericidally active alcohols and carboxylic acids can be used in concentrations considerably lower than their typical use concentrations. In numerical terms, these in-use concentrations may vary within wide limits in accordance with the very different activity of the bactericidal components, so that concentrations of from 0.01 to 30% by weight, based on the treatment solution as a whole, can be considered for selecting the concentration of the bactericidally active components.

The preferred aliphatic monoalcohols, such as ethanol, n-propanol and isopropanol, are used in concentrations of from 8 to 30% by weight, based on the treatment solution as a whole. Alcohols showing stronger bactericidal activity, for example benzylalcohol, are preferably used in concentrations of from 1 to 3% by weight while bactericidally active carboxylic acids are preferably used in concentrations of from 0.01 to 3% by weight, based in each case on the treatment solution as a whole.

The alkyl glycosides used as potentiating agents in accordance with the invention are known from the prior art, for example from the publications cited above. They are prepared by direct reaction from fatty alcohols and sugars, again in known manner. One or more alkyl glycosides containing in the saccharide portion a glycoside residue (alkyl monoglycosides) or several glycoside residues (alkyl oligoglycosides) are used in admixture with the bactericidally active alcohols or carboxylic acids in accordance with the invention. In the alkyl glycosides used in accordance with the invention, up to 8 saccharide residues are attached to one another by glycoside bonds and the alkyl mono- or oligoglycosides formed therefrom are mixed with bactericidally active alcohols or carboxylic acids of the type set forth above. Alkyl monoglycosides containing from 1 to 3 saccharide residues attached to one another by glycoside bonds are preferably used. The saccharide residues can be of any type, although alkyl glycosides containing from 1 to 3 glucose or maltose residues in the glucoside portion are preferably used.

The alkyl portion of the alkyl glycosides used in admixture with bactericidally active alcohols or carboxylic acids in accordance with the invention contain $C_1$–$C_{18}$ alkyl radicals of the type known from synthetic fatty alcohols and/or fatty alcohols emanating from natural sources. The alkyl portion preferably contains $C_6$–$C_{18}$ alkyl radicals. The fatty alcohols on which these alkyl glycosides are based are inexpensively available from natural sources.

With respect to the alkyl glycosides used in admixture with the bactericidally active alcohols or carboxylic acids in accordance with the invention, the indication of the number of saccharide residues should be regarded—as usual—as a statistical mean value based on the distribution typical of these products. Alkyl glycosides containing from 10 to 14 carbon atoms in the alkyl radical and up to 2 glycoside residues and preferably up to 1.5 glycoside residues are particularly suitable for use in accordance with the invention.

Where the alkyl glycosides are used in admixture with the bactericidally active alcohols or carboxylic acids, the concentrations of alkyl glycosides used in accordance with the invention to potentiate the microbicidal effect of the alcohols or carboxylic acids is in the range of from 10 to 2000 ppm and preferably in the range of from 50 to 500 ppm, based on the treatment solution as a whole. In certain mixtures, however, even very low concentrations, for example 10 ppm, in conjunction with corresponding bactericidally active alcohols or carboxylic acids can lead to a distinct improvement in effect. With respect to the use of the above-mentioned antimicrobial agents, it is thus possible to use distinctly lower concentrations of active substance even where small quantities of alkyl glycosides are used as potentiating agents and, at the same time, to obtain a satisfactory microbicidal effect.

This can be seen in particular in the control of gram-positive bacteria. It has been found that, in disinfecting and cleaning preparations active against gram-positive bacteria, it is possible to obtain a particularly distinct increase in the effect of the antiseptic preparations. This is particularly important in the field of personal hygiene preparations, including toothpastes, tooth powders and mouthwashes. However, other disinfecting and cleaning preparations can be distinctly enhanced in their bactericidal activity.

It is precisely in this field that the advantage of using alkyl glycosides in admixture with bactericidally active alcohols or carboxylic acids in accordance with the invention for potentiating the microbicidal effect of these compounds comes into play with particular effect because the bactericidal agents permitted in personal hygiene preparations, for example toothpastes, have hitherto failed to produce a genuine anti-plaque effect in the permitted concentrations. However, it is known that gram-positive bacteria perform a particular function in the formation of plaque and the resulting commencement of dental caries and that particular attention is devoted to their control. The possibility according to the invention of improving activity precisely against gram-positive bacteria provides access here to far more effective agents than have hitherto been available without any need to increase the concentration used.

The bactericidally active disinfecting and cleaning preparations according to the invention, which are characterized by a content in the above-mentioned range of active-substance mixtures of alkyl glycosides of the type mentioned and bactericidal alcohols or carboxylic acids, normally have a pH-value of from 4.5 to 9.5, a preferred pH-range being from 6 to 8. The active-substance combination of alkyl glycosides and bactericidally active alcohols or carboxylic acids used in accordance with the invention is optionally used together with suitable carriers and auxiliary materials which, in turn, may perform known functions in disinfecting or cleaning preparations of the types discussed above. More specifically, the carrier component of an oral hygiene and/or dental care preparation or similar disinfecting and cleaning preparation of this type can be a standard toothpaste, mouthwash, aqueous solution, chewing gum, gel or the like.

For example, dental care or tooth cleaning preparations contain an abrasive polish and, normally, foaming agents, flavorings and sweetners. In addition, toothpastes generally contain humectants, binders and water. Known, suitable polishes are, for example, calcium carbonate, dicalcium orthophosphate dihydrate, calcium pyrophosphate, calcium polymetaphosphate and insoluble sodium polymetaphosphate, aluminium trihydroxide, o-aluminium oxide and silicas, particularly gel silicas and the precipitated silicas. It can be of particular advantage to use abrasives which are compatible with the bactericidally active alcohols and carboxylic acids. Here, too, reference is made to the prior art as represented, for example, by German published application 26 27 548.

The total content of abrasives in the bactericidally active disinfecting and cleaning preparations according to the invention suitable for cleaning teeth can amount to between 0.5 and 95% by weight, based on the tooth cleaning preparation as a whole. The abrasives are normally present in quantities of from 6 to 60% by weight in the case of toothpastes and in quantities of from 20 to 95% by weight in the case of tooth powders.

Tooth cleaning preparations normally contain surfactants as foam generators. Suitable surfactants are the usual non-soap-like, nonionic, cationic, zwitter-ionic and amphoteric organic synthetic surfactants. As already mentioned, however, the alkyl glycosides used in accordance with the invention to enhance activity, of which the surfactant properties are also known from the prior art, are particularly suitable. Suitable nonionic detergents are the condensates of alkylene oxides with organic hydrophobic compounds containing, for example, an aliphatic or alkyl aromatic group. When used in tooth cleaning or dental-care preparations, foam generators are normally present in quantities of from 0.5 to 5% by weight.

If desired, suitable flavorings may also be added to the disinfecting and cleaning preparations according to the invention and in particular to the preparations intended for dental care and oral hygiene. Examples of such flavorings are methyl salicylate, peppermint oil, sassafras oil and aniseed oil. The flavorings are normally used in quantities of from 0.01 to 2.0% by weight. Sweetners may also be used in addition to or instead of the flavorings, normally in quantities of from 0.05 to 2% by weight.

Thickeners which may also be used are the usual thickeners, such as hydroxyethyl cellulose and water-soluble salts of cellulose ethers, natural gums or mucilages. Colloidal inorganic components, such as finely divided silicon dioxide or colloidal magnesium aluminium silicate, may also be used. With regard to the possible use of substances such as these, reference is made to the relevant prior-art literature cited above. Thickeners are normally used in quantities of from 0.1 to 5.0% by weight, based on the particular preparation, for example the toothpaste. If desired, humectants may also be added. Suitable humectants are, for example, glycerol, sorbitol and other polyhydric alcohols and mixtures thereof. They may be present in quantities of from about 1 to 50% by weight of the particular preparation, for example the toothpaste, and are normally mixed with water.

Mouthwashes normally contain a water/ethyl alcohol solution and, if desired, other components, such as flavorings, sweetners and humectants of the type mentioned above. According to the invention, they contain the above-described combination of antimicrobially active alcohols or carboxylic acids and alkyl glycosides, the active components being present in the above-mentioned quantities.

The invention is illustrated but not limited by the following examples.

EXAMPLES

A. Microbicidal Activity

The microbicidal activity of the mixture of bactericidally active alcohols or carboxylic acids and alkyl glycosides used in accordance with the invention was determined against the following test bacteria suspensions:

(a) *Staphylococcus aureus:* $2 \times 10^9$ bacteria/ml
(b) *Streptococcus mutans:* $1 \times 10^9$ bacteria/ml;
(c) *Escherichia coli:* $2 \times 10^9$ bacteria/ml;
(d) *Candida albicans:* $2 \times 10^8$ bacteria/ml The destruction times of the combinations to be tested were determined by the suspension test. Using water having a hardness of 17° Gh., test solutions were prepared which contained the quantities of alkyl glycoside indicated in the Tables and the quantities of bactericidally active alcohol or carboxylic acid likewise indicated. In addition, comparison solutions were prepared which, on the one hand, contained only bactericidally active compounds in the concentrations indicated and, on the other hand, only alkyl glycosides in a concentration of 10,000 ppm.

At room temperature, quantities of 0.1 ml of the test bacteria suspension were pipetted into test tubes and mixed with quantities of 10 ml of the test or comparison solutions described above. After different contact times (up to 60 minutes), quantities of approximately 0.05 ml of material were removed from the test tubes by means of an inoculating ring and spread onto a nutrient agar containing 3% of Tween 80 as de-inhibitor and 0.3% of lecithin. The nutrient medium for bacteria (a) to (d) consisted of 2.5% by weight Standard-I-Bouillon (Merck) and, for bacteria (e), of Würze-Bouillon pH 5 (Merck). The nutrient media each contained 1.2% by weight of agar for gelatinization. The samples were incubated at 37° C. and 30° C., respectively. After 3 days at the earliest, the culture were macroscopically examined for growth and the destruction time or residual bacteria content determined in this way.

In the following Table: "+" means less than 50, "++" means less than 200 and "+++" more than 200 residual bacteria after a contact time of 60 minutes.

EXAMPLE 1

A semi-quantitative suspension test was carried out to determine the increase in the microbicidal activity of alcohols produced by admixture with A. $C_{12/14}$ alkyl oligoglucoside (degree of oligomerization 1.5), of which the alkyl radicals are derived from an n-dodecanol/n-tetradecanol mixture in a ratio by weight of 70:30 and B. undecenyl monoglucoside in quantities of 0, 100, and 1000 ppm. The concentrations of microbicidal agent are shown in column 2 of Tables 1 and 2 below. The microbicidal effect of the alcohols was tested against Staphylococcus aureus (a), Escherichia coli (d) and Candica albicans (e). The results (destruction times and residual bacteria content after 60 minutes' contact with the active-substance combination) are shown in Tables 1 and 2 below.

TABLE 1

Semi-quantitative suspension test
Enhancement of the microbicidal effect of alcohols by combination with alkyl glycoside (A)

| Active Substance | Active Substance conc. (%) | Staph. aureus Glucoside concentration | | | E. coli Glucoside concentration | | | Cand. albicans Glucoside concentration | | |
|---|---|---|---|---|---|---|---|---|---|---|
| | | 0 ppm | 100 ppm | 1000 ppm | 0 ppm | 100 ppm | 1000 ppm | 0 ppm | 100 ppm | 1000 ppm |
| Ethanol | 30 | 60 | ≦5 | ≦5 | 60 | ≦5 | ≦5 | 15 | 15 | 60 |
| | 25 | 60 | ≦5 | ≦5 | ++ | 60 | 60 | + | 15 | 60 |
| | 20 | +++ | 15 | ≦5 | ++ | ++ | +++ | +++ | + | + |
| n-Propanol | 20 | 15 | ≦5 | ≦5 | 15 | ≦5 | ≦5 | 15 | ≦5 | ≦5 |
| | 16 | 15 | ≦5 | ≦5 | 15 | ≦5 | ≦5 | 60 | ≦5 | ≦5 |
| | 12 | +++ | ≦5 | ≦5 | +++ | 60 | ≦5 | +++ | 15 | 15 |
| i-Propanol | 20 | 15 | ≦5 | ≦5 | 15 | ≦5 | 15 | 60 | ≦5 | ≦5 |
| | 16 | 15 | ≦5 | 15 | 60 | 60 | 60 | + | 15 | 15 |
| | 12 | 60 | 15 | 15 | +++ | +++ | +++ | +++ | ++ | + |
| Benzyl-alcohol | 2.5 | ≦5 | ≦5 | ≦5 | ≦5 | ≦5 | 15 | 60 | 15 | ≦5 |
| | 2.0 | ≦5 | ≦5 | 15 | ≦5 | ≦5 | 15 | +++ | + | ++ |

TABLE 1-continued

Semi-quantitative suspension test
Enhancement of the microbicidal effect of alcohols by combination with alkyl glycoside (A)

| Active Substance | Active Substance conc. (%) | Staph. aureus Glucoside concentration | | | E. coli Glucoside concentration | | | Cand. albicans Glucoside concentration | | |
|---|---|---|---|---|---|---|---|---|---|---|
| | | 0 ppm | 100 ppm | 1000 ppm | 0 ppm | 100 ppm | 1000 ppm | 0 ppm | 100 ppm | 1000 ppm |
| | 1.5 | 60 | 15 | 15 | 60 | 60 | +++ | +++ | +++ | +++ |

Figures in the Table = destruction time in minutes
+, ++, +++, = increasing residual bacteria content after a contact time of 60 minutes

TABLE 2

Semi-quantitative suspension test
Enhancement of the microbicidal effect of alcohols by combination with alkyl glycoside (B)

| Active Substance | Active Substance conc. (%) | Staph. aureus Glucoside concentration | | | E. coli Glucoside concentration | | | Cand. albicans Glucoside concentration | | |
|---|---|---|---|---|---|---|---|---|---|---|
| | | 0 ppm | 100 ppm | 1000 ppm | 0 ppm | 100 ppm | 1000 ppm | 0 ppm | 100 ppm | 1000 ppm |
| Ethanol | 30 | 60 | ≦5 | ≦5 | 60 | 15 | ≦5 | 15 | 15 | 15 |
| | 25 | 60 | ≦5 | ≦5 | ++ | + | 15 | + | 60 | 15 |
| | 20 | +++ | 15 | ≦5 | ++ | ++ | 60 | +++ | +++ | 60 |
| n-Propanol | 20 | 15 | ≦5 | ≦5 | 15 | ≦5 | ≦5 | 15 | ≦5 | ≦5 |
| | 16 | 15 | ≦5 | ≦5 | 15 | ≦5 | ≦5 | 60 | ≦5 | ≦5 |
| | 12 | +++ | ≦5 | ≦5 | +++ | ≦5 | ≦5 | +++ | 15 | ≦5 |
| i-Propanol | 20 | 15 | ≦5 | ≦5 | 15 | ≦5 | ≦5 | 60 | ≦5 | ≦5 |
| | 16 | 15 | ≦5 | ≦5 | 60 | 15 | 15 | + | 60 | 15 |
| | 12 | 60 | ≦5 | 15 | +++ | +++ | ++ | +++ | + | + |
| Benzyl-alcohol | 2.5 | ≦5 | ≦5 | ≦5 | ≦5 | ≦5 | ≦5 | 60 | 15 | 60 |
| | 2.0 | ≦5 | ≦5 | ≦5 | ≦5 | ≦5 | ≦5 | +++ | ++ | 60 |
| | 1.5 | 60 | 60 | ≦5 | 60 | 60 | 60 | +++ | +++ | +++ |

Figures in the Table = destruction time in minutes
+, ++, +++, = increasing residual bacteria content after a contact time of 60 minutes Result:

As can be seen from Tables 1 and 2, distinct enhancements of the microbicidal effect of the particular alcohols are obtained where alkyl glycosides are used in admixture with those alcohols. This enhancement is clearest in the case of ethanol and n-propanol.

EXAMPLE 2

A semi-quantitative suspension test was carried out to determine the increase in the microbicidal effect of organic carboxylic acids produced by admixture with the alkyl glycosides A. $C_{12/14}$ alkyl oligoglucoside (degree of oligomerization 1.4), of which the alkyl radicals are derived from an n-dodecanol/n-tetradecanol mixture in a ratio by weight of 70:30 and B. undecenyl monoglucoside.

In this test, the mixtures were tested for their microbicidal effect against *Staphylococcus aureus* (a), *Escherichia coli* (d) and *Candida albicans* (e). The concentrations of the microbicidally active carboxylic acids are shown in Column 2 of Tables 3 and 4. The carboxylic acids used were benzoic acid, lactic acid, propionic acid (sodium salt), salicylic acid and sorbic acid. The results are shown in Tables 3 and 4 below.

TABLE 3

Semi-quantitative suspension test
Enhancement of the microbicidal effect of organic acids by combination with alkyl glycoside (A)

| Active Substance | Active Substance conc. (%) | pH-Value | Staph. aureus Glucoside concentration | | | E. coli Glucoside concentration | | | Cand. albicans Glucoside concentration | | |
|---|---|---|---|---|---|---|---|---|---|---|---|
| | | | 0 ppm | 100 ppm | 1000 ppm | 0 ppm | 100 ppm | 1000 ppm | 0 ppm | 100 ppm | 1000 ppm |
| Benzoic acid | 1.0 | 2.9 | 15 | ≦5 | ≦5 | + | ≦5 | 15 | 60 | 15 | 15 |
| | 0.3 | 2.9 | 60 | ≦5 | ≦5 | +++ | 15 | 15 | +++ | + | +++ |
| | 0.1 | 2.9 | + | ≦5 | 15 | +++ | ++ | ++ | +++ | ++ | +++ |
| Lactic acid | 2.0 | 1.9 | 60 | | | 60 | | | +++ | | |
| | 1.0 | 2.1 | + | ≦5 | 60 | + | 15 | 60 | +++ | +++ | +++ |
| | 0.5 | 2.4 | ++ | 15 | 60 | +++ | 60 | + | +++ | +++ | +++ |
| | 0.1 | 2.7 | | 60 | 60 | | ++ | ++ | | | |
| Salicyclic acid | 1.0 | 2.4 | ≦5 | ≦5 | ≦5 | 15 | ≦5 | 60 | 15 | ≦5 | 15 |
| | 0.3 | 2.4 | ≦5 | ≦5 | ≦5 | 60 | ≦5 | 60 | 15 | ≦5 | 15 |
| | 0.1 | 2.4 | ≦5 | ≦5 | ≦5 | 60 | ≦5 | + | 60 | 15 | 15 |
| Sorbic acid | 2.0 | 2.4 | 60 | ≦5 | ≦5 | ++ | 60 | 15 | +++ | ++ | +++ |
| | 1.0 | 2.6 | 60 | ≦5 | ≦5 | ++ | + | 60 | +++ | +++ | +++ |
| | 0.5 | 2.8 | + | ≦5 | ≦5 | +++ | ++ | + | +++ | +++ | +++ |

Figures in the Table = destruction time in minutes
+, ++, +++, = increasing residual bacteria content after a contact time of 60 minutes

TABLE 4

Semi-quantitative suspension test
Enhancement of the microbicidal effect of organic acids by combination with undecenyl glucoside (B)

| Active Substance | Active Substance conc. (%) | pH-Value | Staph. aureus Glucoside concentration | | | E. coli Glucoside concentration | | | Cand. albicans Glucoside concentration | | |
|---|---|---|---|---|---|---|---|---|---|---|---|
| | | | 0 ppm | 100 ppm | 1000 ppm | 0 ppm | 100 ppm | 1000 ppm | 0 ppm | 100 ppm | 1000 ppm |
| Benzoic acid | 1.0 | 2.9 | 15 | 60 | ≦5 | + | ≦5 | ≦5 | 60 | +++ | 15 |
| | 0.3 | 2.9 | 60 | 60 | ≦5 | ++ | 15 | ≦5 | + | +++ | + |
| | 0.1 | 2.9 | + | 60 | ≦5 | ++ | + | ≦5 | +++ | +++ | + |
| Lactic acid | 2.0 | 1.9 | +++ | | | 15 | | | + | | |
| | 1.0 | 2.1 | +++ | ≦5 | | + | 15 | | +++ | +++ | +++ |
| | 0.5 | 2.4 | +++ | + | ≦5 | ++ | + | | +++ | +++ | +++ |
| | 0.1 | 2.7 | | ++ | 15 | | ++ | 15 | | +++ | +++ |
| | 0.05 | | | | 60 | | | + | | | |
| | 0.025 | 3.1 | | | 60 | | | +++ | | | |
| Salicyclic acid | 1.0 | 2.4 | ≦5 | ≦5 | ≦5 | 60 | ≦5 | ≦5 | 15 | ≦5 | ≦5 |
| | 0.3 | 2.4 | 60 | ≦5 | ≦5 | 60 | ≦5 | ≦5 | 15 | ≦5 | ≦5 |
| | 0.1 | 2.4 | 60 | 15 | 15 | 60 | 15 | 15 | 60 | 15 | ≦5 |
| Sorbic acid | 2.0 | 2.4 | 15 | 15 | ≦5 | + | 60 | ≦5 | +++ | +++ | 60 |
| | 1.0 | 2.6 | 60 | 60 | ≦5 | ++ | 60 | ≦5 | +++ | +++ | 60 |
| | 0.5 | 2.8 | + | 60 | ≦5 | +++ | + | ≦5 | +++ | +++ | ++ |

Figures in the Table = destruction time in minutes
+, ++, +++, = increasing residual bacteria content after a contact time of 60 minutes Result:
All the carboxylic acids set forth above produce enhancements of effect; enhancement factors of up to 10 being observed.

EXAMPLE 3

The semi-quantitative suspension test of Example 2 was repeated with benzoic acid and lactic acid as microbicidal carboxylic acids against *Staphylococcus aureus* (a) and *Escherichia coli* (e), different active-substance concentrations being used in the mixtures compared with Example 2. The results are shown in Table 5 below.

TABLE 5

Semi-quantitative suspension test
Active substances in combination with 1000 ppm undecencyl glucoside (B) and without glucoside

| Active Substance | Active Substance conc (%) | Staph. aureus Glucoside concentration | | E. coli Glucoside concentration | |
|---|---|---|---|---|---|
| | | 0 ppm | 1000 ppm | 0 ppm | 1000 ppm |
| Benzoic acid | 0.2 | 60 | 5 | ++ | 5 |
| | 0.1 | +++ | 5 | +++ | 15 |
| | 0.05 | +++ | 5 | +++ | 60 |
| Lactic acid | 0.5 | +++ | 5 | +++ | 5 |
| | 0.25 | +++ | 5 | +++ | 5 |
| | 0.1 | +++ | 15 | +++ | 5 |
| Control without active substance | — | +++ | ++ | +++ | +++ |

Figures in the Table = destruction time in minutes
+, ++, +++ = increasing residual bacteria content after a contact time of 60 minutes.

Result:
Even at concentrations of the microbicidal components in the ranges shown in Table 5, the addition of 1000 ppm of the glucoside produced a considerable increase in the microbicidal activity of benzoic acid and lactic acid. Whereas, without any addition of glucoside, the benzoic acid and lactic acid show weak microbicidal effects at 2000 and 5000 ppm, satisfactory destruction of the test bacteria is obtained even at bactericide concentrations of 500 to 1000 ppm by addition of 1000 ppm of the glucoside.

We claim:
1. A bactericidally active composition comprising:
A. a bactericidal quantity of at least one bactericidally active alcohol or carboxylic acid or its water-soluble salt; and
B. an activity potentiating quantity of at least one alkyl glycoside.

2. The composition of claim 1 in the form of an aqueous solution.

3. The composition of claim 1 wherein component A is present in the amount of from about 0.01 to about 30% by weight of the composition.

4. The composition of claim 3 wherein component B is present in the amount of from about 10 to about 2000 ppm, based on the weight of the composition.

5. The composition of claim 3 wherein component B is present in the amount of from about 50 to about 500 ppm, based on the weight of the composition.

6. The composition of claim 1 wherein component A is at least one aliphatic alcohol or phenyl-aliphatic alcohol, wherein such alcohols contain one or more hydroxyl groups.

7. The composition of claim 6 wherein component A is at least one $C_1$–$C_6$ straight-chain or branched-chain aliphatic alcohol, unsubstituted or mono- or disubstituted with substituents from the group consisting of Cl, Br, and $NO_2$.

8. The composition of claim 7 wherein in component A the at least one alcohol contains from 2 to 4 carbon atoms.

9. The composition of claim 8 wherein in component A the at least one alcohol is 2-bromo-2-nitro-1,3-propane diol.

10. The composition of claim 8 wherein component A is one or more of ethanol, n-propanol, and isopropanol.

11. The composition claim 6 wherein component A is at least one straight chain phenyl-aliphatic alcohol containing from 1 to 3 carbon atoms in the alkylene radical, and which alkylene radical is unsubstituted or substituted with 1 or 2 substituents selected from the group consisting of Cl, Br, and $NO_2$.

12. The composition of claim 10 wherein component A is benzyl alcohol.

13. The composition of claim 1 wherein component A is a mixture of at least one alcohol and at least one carboxylic acid or water soluble salt thereof.

14. The composition of claim 1 wherein component A is at least one aliphatic or aromatic carboxylic acid containing one or more carboxyl groups, or water soluble salt thereof.

15. The composition of claim 14 wherein component A is at least one $C_1$-$C_{12}$ straight chain or branched chain, saturated or olefinically unsaturated aliphatic monocarboxylic or dicarboxylic acid, or water soluble salt thereof.

16. The composition of claim 15 wherein said carboxylic acid is unsubstituted or is substituted with 1 or 2 substituents selected from the group consisting of Cl, Br, $NO_2$ and OH.

17. The composition of claim 15 wherein said carboxylic acid is a $C_3$-$C_6$ acid or water soluble salt thereof.

18. The composition of claim 17 wherein said at least one carboxylic acid is mono- or poly-olefinically unsaturated.

19. The composition of claim 17 wherein component A is at least one of propionic acid, butyric acid, valeric acid, or a water soluble salt thereof.

20. The composition of claim 18 wherein component A is sorbic acid, or water soluble salt of sorbic acid, or a mixture thereof.

21. The composition of claim 16 wherein component A is lactic acid, a water soluble salt of lactic acid, or a mixture thereof.

22. The composition of claim 14 wherein component A is at least one monocyclic aromatic carboxylic acid which is unsubstituted or substituted by 1 or 2 substituents selected from the group consisting of Cl, Br, and OH, or a water soluble salt thereof.

23. The composition of claim 22 wherein component A is at least one of benzoic acid, salicylic acid, or a water soluble salt thereof.

24. The composition of claim 14 wherein the water soluble salt is the sodium salt.

25. The composition of claim 1 wherein component B is at least one alkyl monoglycoside or alkyl oligoglycoside containing from 2 to 8 saccharide residues attached by glycoside bonds.

26. The composition of claim 25 wherein component B is at least one alkyl glycoside containing from 1 to 3 saccharide residues attached by glycoside bonds.

27. The composition of claim 26 wherein component B is at least one alkyl glycoside containing from 1 to 3 glucose or maltose residues.

28. The composition of claim 25 wherein the at least one alkyl mono- or oligoglycoside contains from 1 to 18 carbon atoms in the alkyl group.

29. The composition of claim 28 wherein from 6 to 18 carbon atoms are present in the alkyl group.

30. The composition of claim 3 wherein the composition is in the form of a personal hygiene preparation.

31. The composition of claim 30 wherein the composition is a toothpaste, tooth powder, or mouthwash.

* * * * *

UNITED STATES PATENT AND TRADEMARK OFFICE
CERTIFICATE OF CORRECTION

PATENT NO.  : 4,920,100

DATED       : April 24, 1990

INVENTOR(S) : Rudolf Lehmann et al.

It is certified that error appears in the above-identified patent and that said Letters Patent is hereby corrected as shown below:

On the face page, at item [22], the date filed should read --June 9, 1987--.

Signed and Sealed this

Eighteenth Day of June, 1991

Attest:

*Attesting Officer*

HARRY F. MANBECK, JR.

*Commissioner of Patents and Trademarks*